(12) United States Patent
Takahashi et al.

(10) Patent No.: US 6,753,901 B1
(45) Date of Patent: Jun. 22, 2004

(54) VIDEO-SIGNAL PROCESSING DEVICE CONNECTABLE TO AN ELECTRONIC ENDOSCOPE

(75) Inventors: Akihiro Takahashi, Tokyo (JP); Kouhei Iketani, Tokyo (JP)

(73) Assignee: PENTAX Corporation, Tokyo (JP)

( * ) Notice: Subject to any disclaimer, the term of this patent is extended or adjusted under 35 U.S.C. 154(b) by 694 days.

(21) Appl. No.: 08/831,872

(22) Filed: Apr. 2, 1997

(30) Foreign Application Priority Data

Apr. 3, 1996 (JP) .......................................... P8-106183

(51) Int. Cl.[7] .......................... H04N 7/18; A61B 7/045
(52) U.S. Cl. .......................... 348/65; 348/71; 600/109
(58) Field of Search .............................. 348/45, 46, 65, 348/72, 75, 73; 600/76, 109; 362/803; 358/37, 98, 209; 307/119; 128/664, 660.07; 250/201; H04N 7/18; A61B 1/045

(56) References Cited

U.S. PATENT DOCUMENTS

| | | | | |
|---|---|---|---|---|
| 4,473,841 A | * | 9/1984 | Murakoshi et al. ............ 358/98 |
| 4,653,478 A | * | 3/1987 | Nagasaki et al. ............ 362/803 |
| 4,853,772 A | * | 8/1989 | Kikuchi ........................ 358/98 |
| 4,928,172 A | * | 5/1990 | Uehara et al. ................. 358/98 |
| 4,950,880 A | * | 8/1990 | Hayer .......................... 250/201 |
| 4,953,011 A | * | 8/1990 | Mori et al. .................... 358/37 |
| 5,138,458 A | * | 8/1992 | Nagasaki et al. ............ 358/209 |
| 5,293,872 A | * | 3/1994 | Alfano et al. ................ 128/664 |
| 5,305,098 A | * | 4/1994 | Matshunaka et al. ......... 348/65 |
| 5,349,653 A | * | 9/1994 | Kurkawa et al. ............ 395/500 |
| 5,554,893 A | * | 9/1996 | Oku ........................... 307/119 |
| 5,583,566 A | * | 12/1996 | Kanno et al. .................. 348/72 |
| 5,588,434 A | * | 12/1996 | Fujimoto ............... 128/660.07 |
| 5,675,378 A | * | 10/1997 | Takasugi et al. .............. 348/65 |
| 5,877,802 A | * | 3/1999 | Takahashi et al. ............ 348/71 |
| 5,902,230 A | * | 5/1999 | Takahashi et al. .......... 600/109 |

* cited by examiner

*Primary Examiner*—Tung Vo
(74) *Attorney, Agent, or Firm*—Greenblum & Bernstein, P.L.C.

(57) ABSTRACT

A video-signal processing device is connectable to an electronic endoscope for feeding at least one kind of electric analog video signal from the electronic endoscope to a peripheral equipment. The video-signal processing device has a photo-coupler or a transformer coupler for making it possible to input the electric analog color video signal from the electronic endoscope to the video-signal processing device, whereby the electronic endoscope is electrically insulated from the peripheral equipment for an electrical security. Also, the video-signal processing device has an analog-to-digital converter for converting the electric analog video signal into a parallel electric digital video signal, a parallel-to-serial converter for converting the parallel electric digital video signal into a serial electric digital video signal, and an electrical-optical converter for converting the serial electric digital video signal into a serial optical digital video signal.

16 Claims, 11 Drawing Sheets

VIDEO-SIGNAL PROCESSING DEVICE CONNECTABLE TO AN ELECTRONIC ENDOSCOPE

BACKGROUND OF THE INVENTION

1. Field of the Invention

The present invention relates to a video-signal processing device connectable to an electronic endoscope, and more particularly relates to a video-signal processing device that intervenes between an electronic endoscope and peripheral equipment such as a television monitor, a video tape recorder, a printer, a video-image processing computer, and so on.

2. Description of the Related Art

The described electronic endoscope comprises a flexible conduit and a video processor to which the flexible conduit is detachably joined.

The flexible conduit has an objective lens system provided at the distal end thereof, and a solid state image sensor such as a CCD (charge-coupled device) associated therewith. An object to be photographed is focused, as an optical image, on a light receiving surface of the CCD image sensor by the objective lens system. The optical image is converted into analog image-pixel signals by the CCD image sensor, and the analog image-pixel signals are successively read out of the image sensor by a CCD driver circuit.

Also, the flexible conduit has an optical guide provided within, and the optical guide terminates at a light-emitting end face at the distal end of the flexible conduit. The video processor also includes an optical guide. When the flexible conduit is joined to the video processor, one end of the optical guide of the video processor is connected to a proximal (base) end of the optical guide of the flexible conduit.

The video processor of the electronic endoscope also has a light source and a collective lens system associated therewith, and light rays emitted from the light source are focused on the other end face of the optical guide of the video processor by the collective lens system. Thus, a front area of the distal end of the flexible conduit is illuminated by the light rays emitted from the light-emitting end face of the optical guide of the flexible conduit.

For reproduction of a photographed image as a color image, for example, an RGB field sequential type color imaging system is introduced in the electronic endoscope. Namely, a rotary RGB color filter is intervened between the light source and the inner end face of the optical guide of the video processor, and the RGB color filter is rotated at a given frequency of rotation. In this manner, an object to be photographed is sequentially illuminated by red light rays, green light rays, and blue light rays. Thus, a red optical image, a green optical image, and a blue optical image are focused on the light receiving surface of the CCD image sensor at given time intervals.

Analog color-image-pixel signals successively read from the CCD image sensor by the CCD driver circuit are fed to the video processor, which processes the analog color-image pixel signals to thereby produce a color video signal. Usually, the video processor of the electronic endoscope is connected to a medical TV monitor designed to ensure electrical security, and a photographed image is reproduced on the medical TV monitor on the basis of the color video signal fed from the video processor thereto.

Nevertheless, the electronic endoscope may be connected to a consumer TV monitor at medical site, but in general the consumer TV monitor is not designed to ensure electrical security i.e., "electrical security" being both confidentiality and to insulate a patient from stray current on the signal line.

On the other hand, it is sometimes described to connect an electronic endoscope to other peripheral equipment (such as a video tape recorder, a printer, an image-processor and so on) other than a TV monitor. To this end, the video processor of the electronic endoscope is arranged to output at least two kinds of color video signals. However, in this case, the peripheral equipment are not designed to ensure electrical security.

Furthermore, a user may want to connect the electronic endoscope to a peripheral remotely located from the electronic endoscope. For example, at a large hospital of more than two buildings, there may be a case where a color video signal must be fed from the electronic endoscope used in a room of a first building to a peripheral located at a room of another building. In this case, the video signal should be fed as a digital video signal from the electronic endoscope to the peripheral because an analog video signal is susceptible to attenuation.

Nevertheless, the feeding of the digital video signal to the remote peripheral is not expedient because an expensive parallel signal cable having a plurality of signal lines must be laid therebetween.

SUMMARY OF THE INVENTION

Therefore, an object of the present invention is to provide a video-signal processing device connectable to an electronic endoscope such that a video signal is fed from the electronic endoscope to a peripheral equipment such as a TV monitor, a video tape recorder, a printer, an image-processor and so on therethrough, wherein the electronic endoscope can be securely insulated electrically from the peripheral equipment, to thereby ensure electrical security and to protect a patient from stray current on the signal lines.

Another object of the present invention is to provide a video-signal processing device of the above-mentioned type, wherein the video signal can be fed from the electronic endoscope to the peripheral equipment without being considerably subjected to attenuation.

In accordance with an aspect of the present invention, there is provided a video-signal processing device connectable to an electronic endoscope for feeding at least one kind of electric analog video signal from the electronic endoscope to a peripheral equipment, the video-signal processing device comprising an insulation coupler for making it possible to input the electric analog video signal from the electronic endoscope to the video-signal processing device, whereby the electronic endoscope is electrically insulated from the peripheral equipment. The insulation coupler may be a photo-coupler or a transformer coupler.

Preferably, the video-signal processing device further comprises: an analog-to-digital converter for converting the electric analog video signal into a parallel electric digital video signal; a parallel-to-serial converter for converting the parallel electric digital video signal into a serial electric digital video signal; and an electric-optical converter for converting the serial electric digital video signal into a serial optical digital video signal.

In accordance with another aspect of the present invention, there is provided a video-signal processing device connectable to an electronic endoscope for feeding at least one kind of analog component-type color video signal composed of at least three electric signal-components from the electronic endoscope to a peripheral equipment, the video-signal processing device comprising respective insulation couplers for making it possible to input the electric signal-components from the electronic endoscope to the video-signal processing device, whereby the electronic endoscope is electrically insulated from the peripheral equipment. The insulation couplers may be a photo-coupler or a transformer coupler.

Preferably, the video-signal processing device comprises: an analog-to-digital converter for converting each of the electric signal-components into a parallel electric digital signal-component; a parallel-to-serial converter for converting the parallel electric digital signal-components into serial electric digital signal-components; and an electric-optical converter for converting the serial electric digital signal-components into serial optical digital signal-components.

The respective electric signal-components may be a red video signal-component, a green video signal-component, and a blue video signal-component. In this case, the video-signal processing device may further comprise a color-conversion analog matrix circuit for producing a luminance signal-component, and two kinds of color-difference signal-components on the basis of the red, green, and blue video signal-components; an analog-to-digital converter for converting each of the luminance signal-component and two kinds of color-difference signal-components into a parallel electric digital signal-component; a parallel-to-serial converter for converting the parallel electric digital signal-components into serial electric digital signal-components; and an electric-optical converter for converting the serial electric digital signal-components into serial optical digital signal-components.

When the respective electric signal-components are a red video signal-component, a green video signal-component, and a blue video signal-component, the video-signal processing device also may further comprise an analog-to-digital converter for converting each of the red, green, and blue video signal-components into a parallel electric digital color signal-component; a color-conversion digital matrix circuit for producing a parallel luminance signal-component, and two kinds of parallel color-difference signal-components on the basis of the parallel digital color signal-components; a parallel-to-serial converter for converting the parallel electric digital signal-components into serial electric digital signal-components; and an electric-optical converter for converting the serial electric digital signal-components into a serial optical digital signal-components.

The respective electric signal-components may be a luminance signal-component, and two kinds of color-difference signal-components. In this case, the video-signal processing device may further comprise an analog-to-digital converter for converting each of the luminance signal-component and two kinds of color-difference signal-components into a parallel electric digital signal-component; a parallel-to-serial converter for converting the parallel electric digital signal-components into serial electric digital signal-components; and an electric-optical converter for converting the serial electric digital signal-components into a serial optical digital signal-components.

In accordance with yet another aspect of the present invention, there is provided a video-signal processing device connectable to an electronic endoscope for feeding at least two kind of electric analog video signals from the electronic endoscope to a peripheral equipment, the video-signal processing device comprising respective two insulation couplers for making it possible to input the two kinds of electric analog video signals from the electronic endoscope to the video-signal processing device, whereby the electronic endoscope is electrically insulated from the peripheral equipment. Each of the insulation couplers may be a photo-coupler or a transformer coupler. Also, one of the two kinds of electric analog video signals is an analog component type color video signal, and the other kind of analog video signal may be a color S-video signal or a composite color video signal.

BRIEF DESCRIPTION OF THE DRAWINGS

The objects and other objects of the present invention will be better understood from the following description, with reference to the accompanying drawings in which.

DESCRIPTION OF THE PREFERRED EMBODIMENTS

Figure 1:
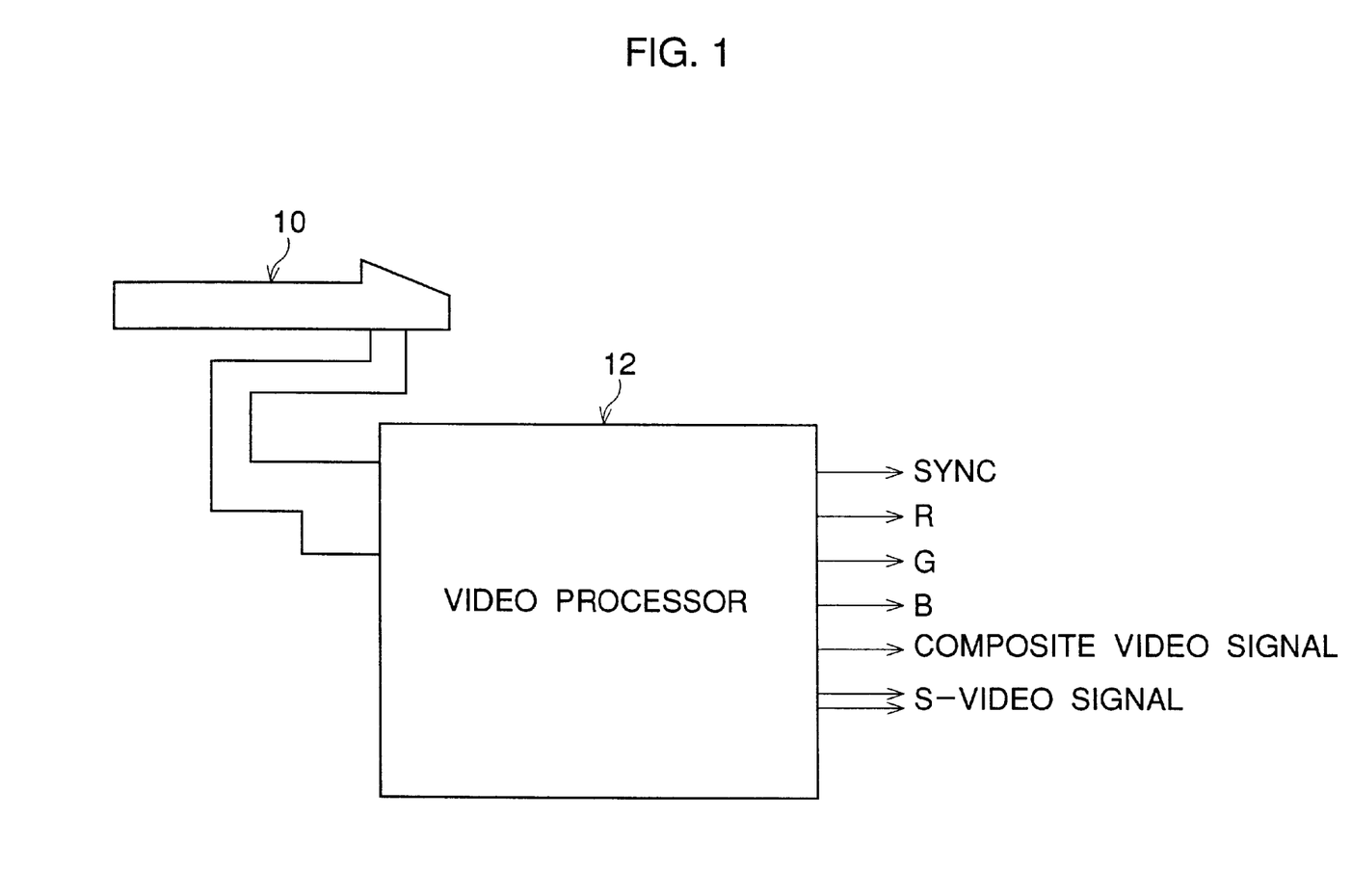
FIG. 1 is a schematic view showing an electronic endoscope to which a video-signal processing device according to the present invention may be connected.

FIG. 1 schematically shows an electronic endoscope, to which a video-signal processing device according to the present invention may be connected. The electronic endoscope includes a flexible conduit 10 and a video processor 12 to which the flexible conduit 10 is detachably joined.

The flexible conduit 10 has an objective lens system (not shown) provided at the distal end thereof, and a solid state image sensor such as a CCD (charge-coupled device not shown) associated therewith. An object to be photographed is focused as an optical image on a light receiving surface of the CCD image sensor by the objective lens system. The optical image is converted into analog image-pixel signals by the CCD image sensor, and the analog image-pixel signals are successively read out of the image sensor by a CCD driver circuit (not shown) therefor.

The flexible conduit 10 has an optical guides (not shown) provided therewithin, and the optical guide may be formed by a bundle of optical fibers. The optical guide terminates at a light-emitting end face at the distal end of the flexible conduit 10. The video processor 12 also includes an optical guide (not shown) provided therein, and this optical guide may be also formed by a bundle of optical fibers. When the flexible conduit 10 is joined to the video processor 12, one end of the optical guide of the video processor 12 is connected to a proximal (base) end of the optical guide of the flexible conduit 10.

The video processor 12 also has a light source (not shown), and a collective lens system (not shown) associated therewith, and light rays emitted from the light source are focused on the other end face of the optical guide of the video processor 12 by the collective lens system. Thus, a front area of the distal end of the flexible conduit 10 is illuminated by the light rays emitted from the light-emitting end face of the optical guide of the flexible conduit 10.

For reproduction of a photographed image as a color image, for example, an RGB field sequential type color imaging system (not shown) is introduced in the electronic endoscope. That is, a rotary RGB color filter intervenes between the light source and the inner end face of the optical guide of the video processor 12, and the RGB color filter is rotated at a given frequency of rotation. An object to be photographed is thereby sequentially illuminated by red light rays, green light rays, and blue light rays. Thus, a red optical image, a green optical image, and a blue optical image are focused on the light receiving surface of the CCD image sensor at given time intervals.

Analog color-image-pixel signals successively read from the CCD image sensor are fed to the video processor 12, and are then subjected to various image-processing such as white-balance processing, gamma-correction processing and so on. In the electronic endoscope shown in FIG. 1, three kinds of color video signals are produced on the basis of the processed color-image-pixel signals, and are output from the video processor 12.

That is, as shown in FIG. 1, as a first kind of color video signal, a component-type color video signal composed of a composite synchronizing signal (SYNC), a red video signal (R), a green video signal (G), and a blue video signal (B) is output from the video processor 12; as a second kind of color video signal, an S-video signal composed of a luminance signal and an amplitude-modulated (AM) color-difference signal is outputted from the video processor 12; and, as a third kind of color video signal, a composite color video signal combined with a luminance signal and an amplitude-modulated (AM) color-difference signal is outputted from the video processor 12.

Figure 2:
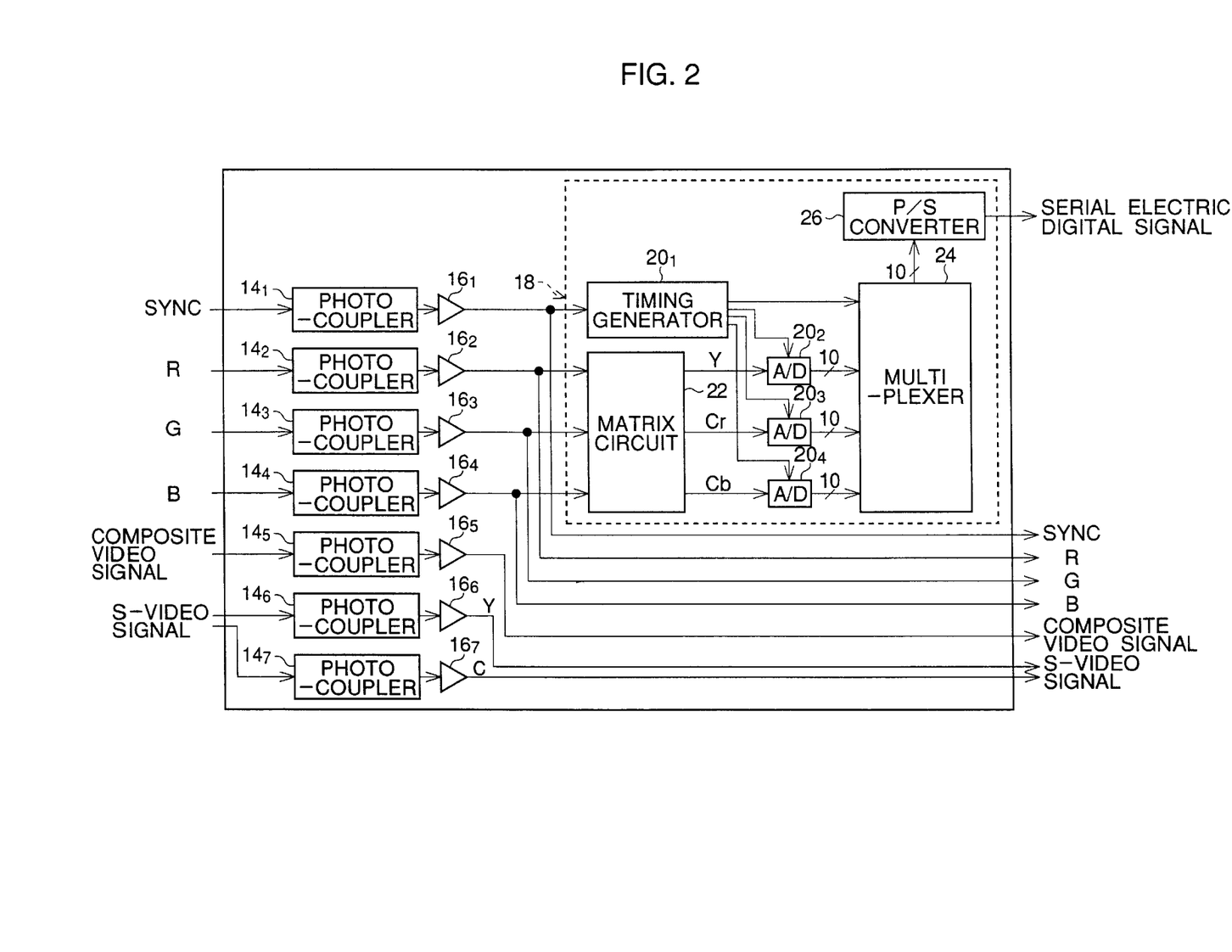
FIG. 2 is a block diagram showing a first embodiment of the video-signal processing device according to the present invention.

FIG. 2 shows a block diagram of a first embodiment of the video-signal processing device according to the present invention, which is connectable to the video processor 12 of the electronic endoscope shown in FIG. 1. The video-signal processing device comprises seven photo-couplers $14_1$ to $14_7$, and, when the video-signal processing device is connected to the video processor 12, the three kinds of video signals output from the video processor 12 are input to the seven photo-couplers $14_1$ to $14_7$.

In particular, the respective composite synchronizing signal (SYNC), red video signal (R), green video signal (G), and blue video signal (B) of the first kind of color video signal (the component-type color video signal) are input to the photo-couplers $14_1$ to $14_4$; the respective luminance signal and amplitude-modulated (AM) color-difference signal of the second kind of color video signal (the S-video signal) are inputted to the photo-couplers $14_6$ and $14_7$; and the third kind of color video signal, i.e., the composite color video signal combined with the luminance signal and the amplitude-modulated (AM) color-difference signal, is input to the photo-coupler $14_5$.

Each of the photo-couplers $14_1$ to $14_7$ converts the inputted electric signal into a photo-signal, and then convents and outputs the photo-signal as an electric signal. Namely, the video-signal processing device is optically coupled to the video processor 12 of the electronic endoscope, whereby the electronic endoscope is electrically insulated from various peripheral equipment connected to the electronic endoscope via the video-signal processing device according to the present invention.

The respective composite synchronizing signal (SYNC), red video signal (R), green video signal (G), and blue video signal (B) output from the photo-couplers $14_1$ to $14_4$ are amplified by the amplifiers $16_1$ to $16_4$, and the amplified signals (SYNC, R, G, B) are directly output, as a component-type video signal, from the video-signal processing device to suitable peripheral equipment connected thereto.

Also, the respective luminance signal and amplitude-modulated (AM) color-difference signal output from the photo-couplers $14_6$ and $14_7$ are amplified by the amplifiers $16_6$ and $14_7$, and the amplified signals are directly output, as an S-video signal, from the video-signal processing device to suitable peripheral equipment connected thereto.

Further, the composite color video signal output from the photo-coupler $14_5$ is amplified by the amplifier $16_5$, and the amplified composite color video-signal is directly output from the video-signal processing device to suitable peripheral equipment.

As is apparent from FIG. 2, the respective amplified composite synchronizing signal (SYNC), red video signal (R), green video signal (G), and blue video signal (B) outputted from the amplifiers $16_1$ to $16_4$ are also inputted to a digital-conversion processing circuit 18 including a timing generator circuit $20_1$; three analog-to-digital (A/D) converters $20_2$, $20_3$, and $20_4$; a color-conversion matrix circuit 22; a multiplexer 24; and a parallel-to-serial(P/S) convertor 26.

In particular, the amplified composite synchronizing signal (SYNC) output from the amplifier $16_1$ is input to the timing generator circuit $20_1$, which produces a horizontal synchronizing signal, a vertical synchronizing signal, and several series of clock pulses having individual frequencies produced on the basis of the input composite synchronizing signal (SYNC).

Also, the amplified red video signal (R), green video signal (G), and blue video signal (B) output from the amplifiers $16_2$, $16_3$, and $16_4$ are input to the color-conversion matrix circuit 22, which produces a luminance signal (Y), and two kinds of color-difference signals $C_r$, $C_b$ ($C_r$=R−Y and $C_b$=B−Y) on the basis of the input color video signals (R, G, and B). Then, the luminance signal (Y), and the two kinds of color-difference signals ($C_r$ and $C_b$) are input to the A/D converters $20_2$, $20_3$, and $20_4$, in which the signals (Y, $C_r$, and $C_b$) are converted into 10-bit digital signals, respectively.

In this embodiment, the sampling of the 10-bit digital luminance signal (Y) from the A/D converter $20_2$ is carried out in accordance with a series of clock pulses of 13.5 MHz output from the timing generator circuit $20_1$. Also, the sampling of each 10-bit digital color-difference signal ($C_r$, $C_b$) from the A/D converters $20_3$ and $20_4$ is carried out in accordance with a series of clock pulses of 6.75 MHz output from the timing generator circuit $20_1$. Namely, the sampling frequency of the digital luminance signal is twice that of each digital color-difference signal ($C_r$, $C_b$).

The 10-bit digital signals (Y, $C_r$, and $C_b$) output from the A/D converters $20_2$, $20_3$, and $20_4$ are input (in parallel) to the multiplexer 24, which output the 10-bit digital signals (Y, $C_r$, and $C_b$) in regular sequence. In this embodiment, for example, the output of the 10-bit digital signals (Y, $C_r$, and $C_b$) may be sequentially carried out in the order of the luminance signal (Y), the color-difference signal ($C_r$), the luminance signal (Y), and the color-difference signal ($C_b$). In this case e.g., the sequential output of the 10-bit digital signals (Y, $C_r$, and $C_b$) is based upon a series of clock pulses of 27 MHz outputted from the timing generator circuit $20_1$. It should be noted that frequency of 2.7 MHz is twice the sampling frequency of 13.5 MHz of the luminance signal (Y).

In this embodiment, over an effective image-period of a horizontal scanning line, the sampling of the digital luminance signals (Y) is carried out 720 times, and each the sampling of the respective color-difference signals ($C_r$ and $C_b$) is carried out 360 times. Namely, a total sampling of 1,440 (720+2*360) samples of the digital signals (Y, $C_r$, and $C_b$) is obtained from the effective image-period of the horizontal scanning line.

Figure 3:
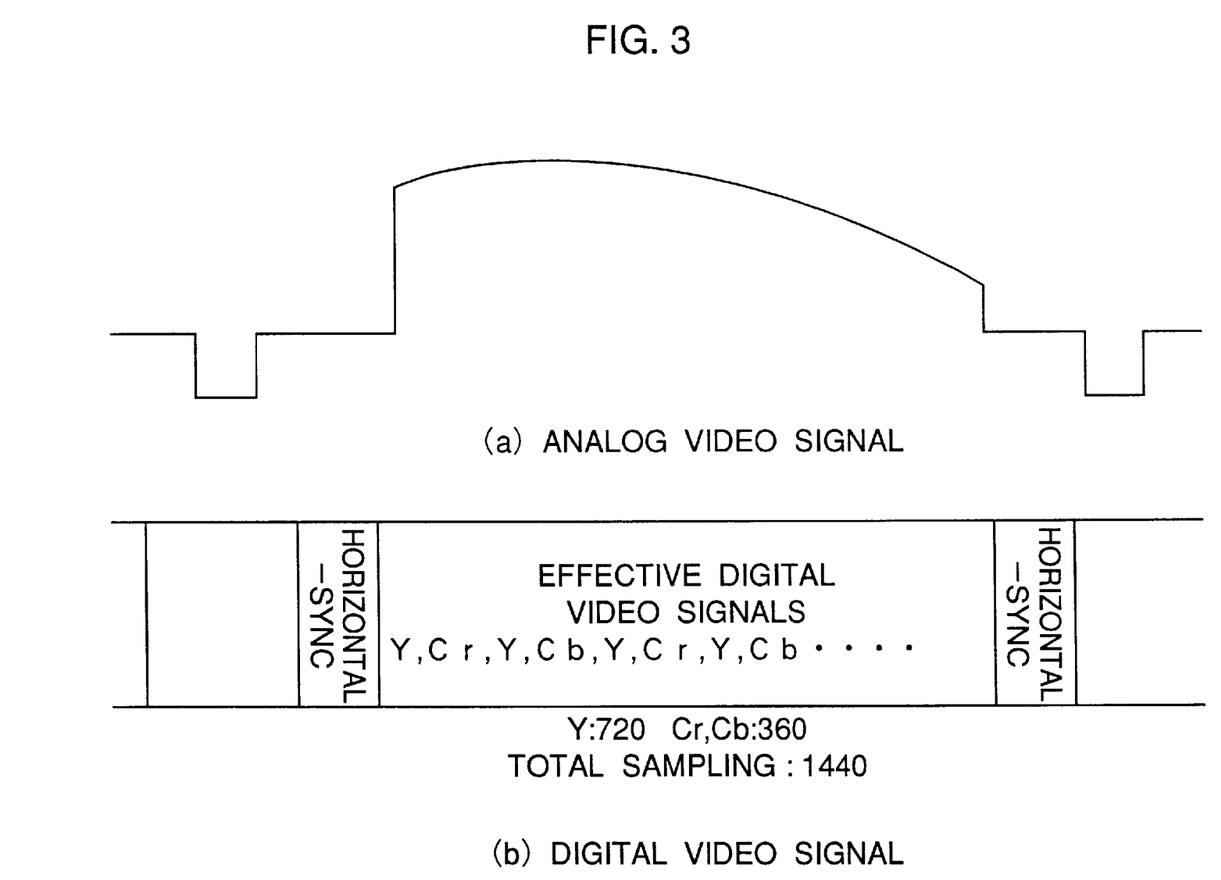
FIG. 3 is a conceptual view showing a relationship between an analog video signal of a horizontal scanning line and sampled digital signals obtained therefrom.

With reference to FIG. 3, a relationship between an analog video signal of a horizontal scanning line and sampled digital signals (Y, $C_r$, and $C_b$) obtained therefrom is conceptually shown.

If the 10-bit digital signal (Y, $C_r$, $C_b$) are directly fed from the multiplexer 24 to a peripheral, the video-signal processing device and the peripheral must be connected to each other through a signal cable having at least eleven signal lines. In this case, ten signal lines of the signal cable would be used for the feeding of the 10-bit digital signal (Y, $C_r$, $C_b$), and the other single line thereof would be necessary for feeding a series of clock pulses having a given frequency. Of course, the use of a parallel signal cable having at least eleven signal lines is not preferable, especially, when the peripheral is not placed in site, i.e., when the peripheral equipment is remote from the place at which the electronic endoscope is used. That is, a parallel signal cable having a plurality of signal lines is expensive.

According to the present invention, the parallel 10-bit digital signal (Y, $C_r$, $C_b$) output from the multiplexer 24 is inputted to the parallel-to-serial (P/S) converter 26, which converts the parallel 10-bit digital signal (Y, $C_r$, $C_b$) into a serial 10-bit digital signal in accordance with a series of clock pulses having a given frequency and output from the timing generator circuit $20_1$.

Figure 4:
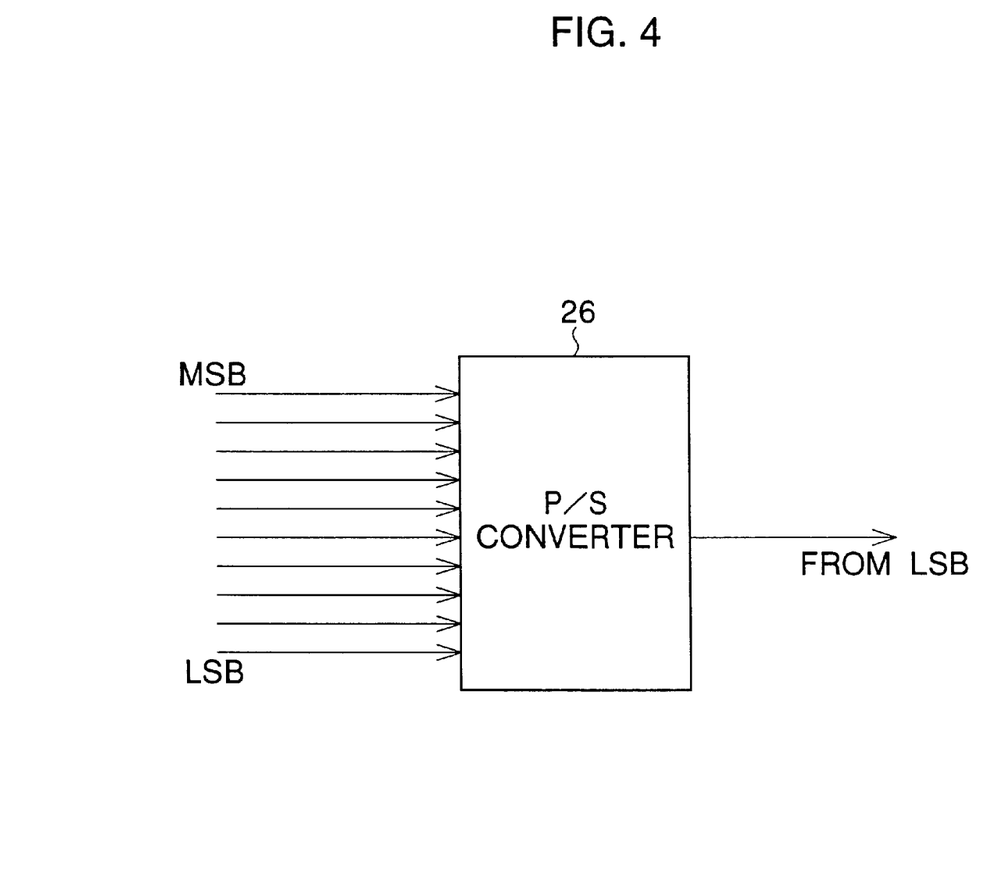
FIG. 4 is a block diagram showing a parallel-to-serial converter used in a digital-conversion processing circuit of the block diagram of FIG. 2.

As shown in FIG. 4, the conversion of the parallel 10-bit digital signal to the serial 10-bit digital signal is carried out in order from the least significant bit (LSB) to the most significant bit (MSB). Namely, the serial 10-bit digital signal is output from the P/S converter 26 in such manner that the least significant bit (LSB) and the most significant bit are defined as a leading bit (MSB) and a trailing bit, respectively.

Figure 5:
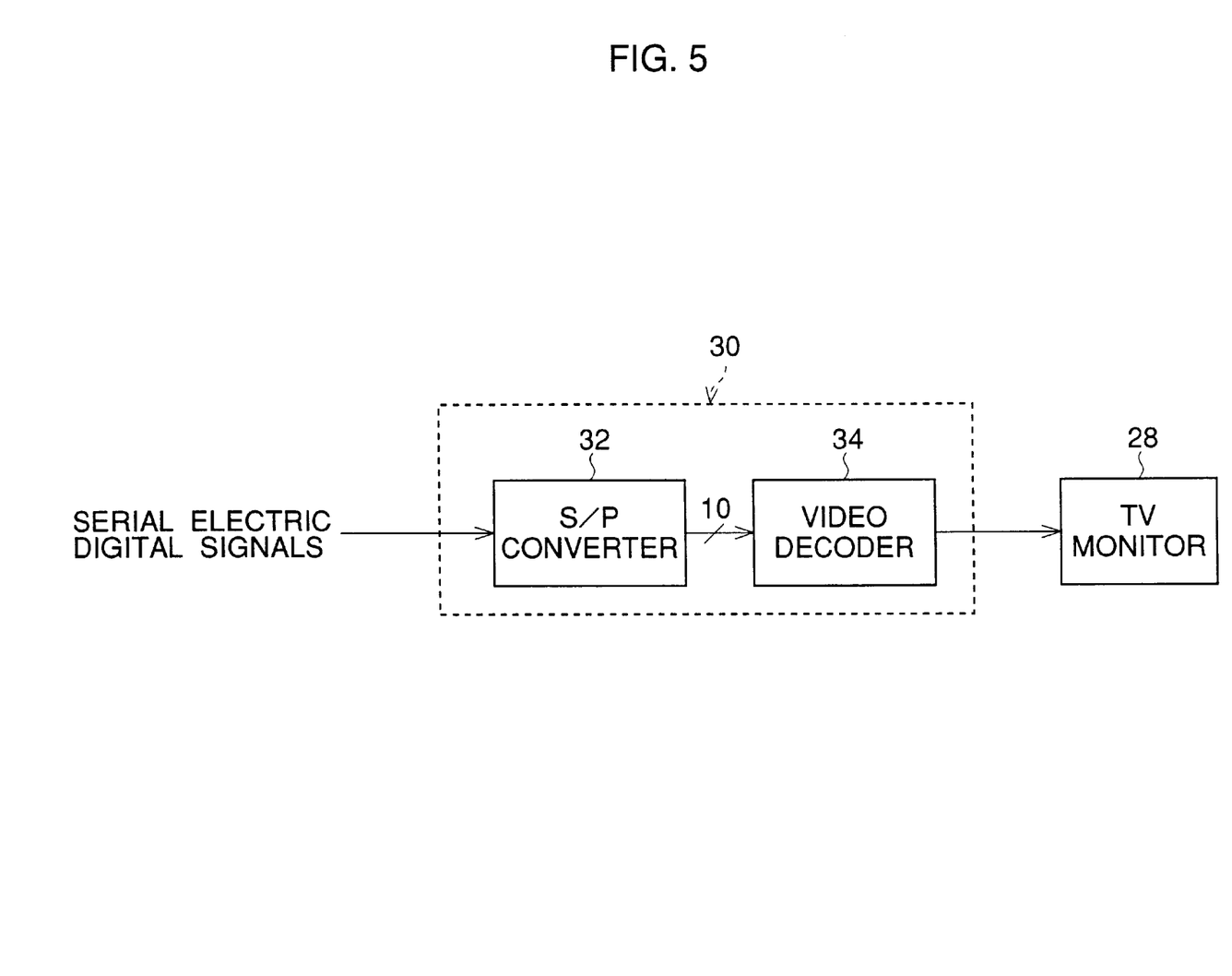
FIG. 5 is a block diagram of an analog-conversion processing device of a TV monitor to be connected to the video-signal processing device of FIG. 2.

FIG. 5 shows a TV monitor 28 as a peripheral, which is connected to the P/S converter 26 of the digital-conversion processing circuit 18 of the video-signal processing device according to the present invention. The system is provided with an analog-conversion processing circuit 30, in which the respective serial digital signals (Y, $C_r$, and $C_b$) fed from the P/S converter 26 thereto are converted into an analog red video signal (R), an analog green video signal (G), and an analog blue video signal (B).

Figure 6:
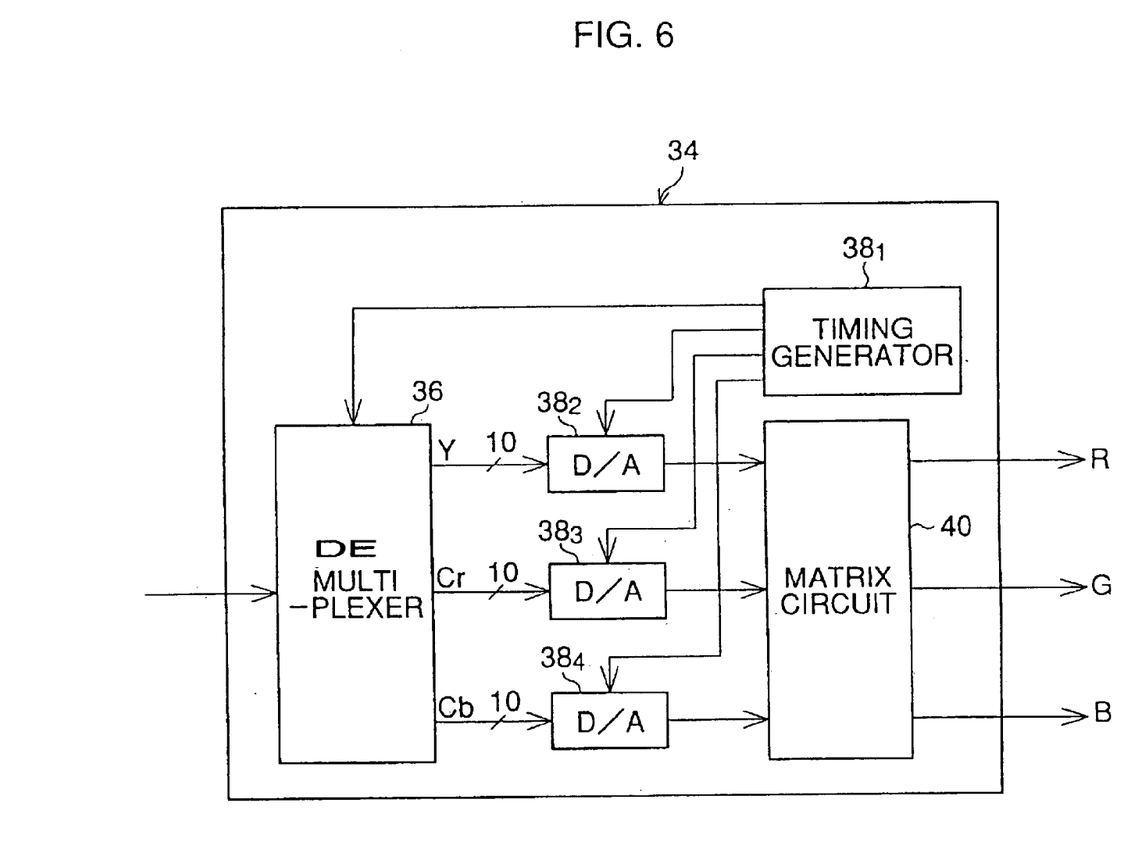
FIG. 6 is a block diagram of a video encoder included in the analog-conversion processing circuit of FIG. 5.

As shown in FIG. 5, the analog-conversion processing circuit 30 comprises a serial-to-parallel (S/P) converter 32 and a video decoder 34. As shown in FIG. 6, the video decoder 34 includes: a multiplexer 36; a timing generator circuit $38_1$; digital-to-analog (D/A) converters $38_2$, $38_3$, and $38_4$; and a color-conversion matrix circuit 40.

As it is apparent from the foregoing, the serial 10-bit digital signals (Y, $C_r$, and $C_b$) are sequentially fed from the P/S converter 26 to the analog-conversion processing circuit 30 in the order of the serial 10-bit digital luminance signal (Y), the serial 10-bit color-difference signal ($C_r$), the serial 10-bit digital luminance signal (Y), and the serial 10-bit digital color-difference signal ($C_b$). The serial 10-bit digital signal (Y, $C_r$, $C_b$) fed to the analog-conversion processing circuit 30 is input to the S/P converter 32, which converts the serial 10-bit digital signal (Y, $C_r$, $C_b$) into a parallel 10-bit digital signal (Y, $C_r$, $C_b$)

The parallel 10-bit digital signals (Y, $C_r$, and $C_b$) outputted from the S/P converter 32 are input to the demultiplexer 36, which distributes the 10-bit digital signals (Y, $C_r$, and $C_b$) to the D/A converters $38_2$, $38_3$, and $38_4$, the respective 10-bit luminance signal (Y), 10-bit color-difference signal ($C_r$), and 10-bit color-difference signal ($C_b$) being input to the D/A converters $38_2$, $38_3$, and $38_4$. The distribution of the 10-bit digital signals (Y, $C_r$, and $C_b$) to the D/A converters $38_2$, $38_3$, and $38_4$ is carried out in accordance with a series of clock pulses having a given frequency, which is output from the timing generator circuit $28_1$ thereto.

The respective D/A converters $38_2$, $38_3$, and $38_4$ convert the 10-bit digital signals (Y, $C_r$, $C_b$) into an analog luminance signal (Y), an analog color-difference signal ($C_r$), and an analog color-difference signal ($C_b$), and the conversion of each 10-bit digital signal (Y, $C_r$, $C_b$) into its analog signal is carried out in accordance with a series of clock pulses having a given frequency, which is output from the timing generator circuit $38_1$, to the D/A converters $38_2$, $38_3$, $38_4$.

The analog signals (Y, $C_r$, and $C_b$) output from the respective D/A converters $38_2$, $38_3$, and $38_4$ are input to the color-conversion matrix circuit 40, in which the analog signals (Y, $C_r$, and $C_b$) are converted into an analog red vide signal (R), an analog green video signal (G), and an analog blue video signal (B). These analog color video signals (R, G, and B) are fed from the color-conversion matrix circuit 40 to the TV monitor 28 to thereby reproduce a color image thereon.

The video-signal processing device as mentioned above intervenes between the electronic endoscope and various peripheral equipment such as a TV monitor, a video tape recorder, a printer, a video-image processing computer and so on. The electronic endoscope is electrically insulated from the peripheral equipment by the photo-couplers $14_1$ to $14_7$ of the video-signal processing device according to the present invention.

According to the present invention, the serial digital video signals (Y, $C_r$, and $C_b$) output from the digital-conversion processing circuit 18 can be fed to the TV monitor 28 through a coaxial cable having a single signal line, which is cheaper than the parallel signal cable having at least eleven single lines as mentioned above. Also, although the TV monitor 28 is remote from the place where the electronic endoscope is used, a clear and proper reproduction of color images on the TV monitor 28 can be ensured, because the video signal is fed to the TV monitor 28 as a digital video signal.

Figure 7:
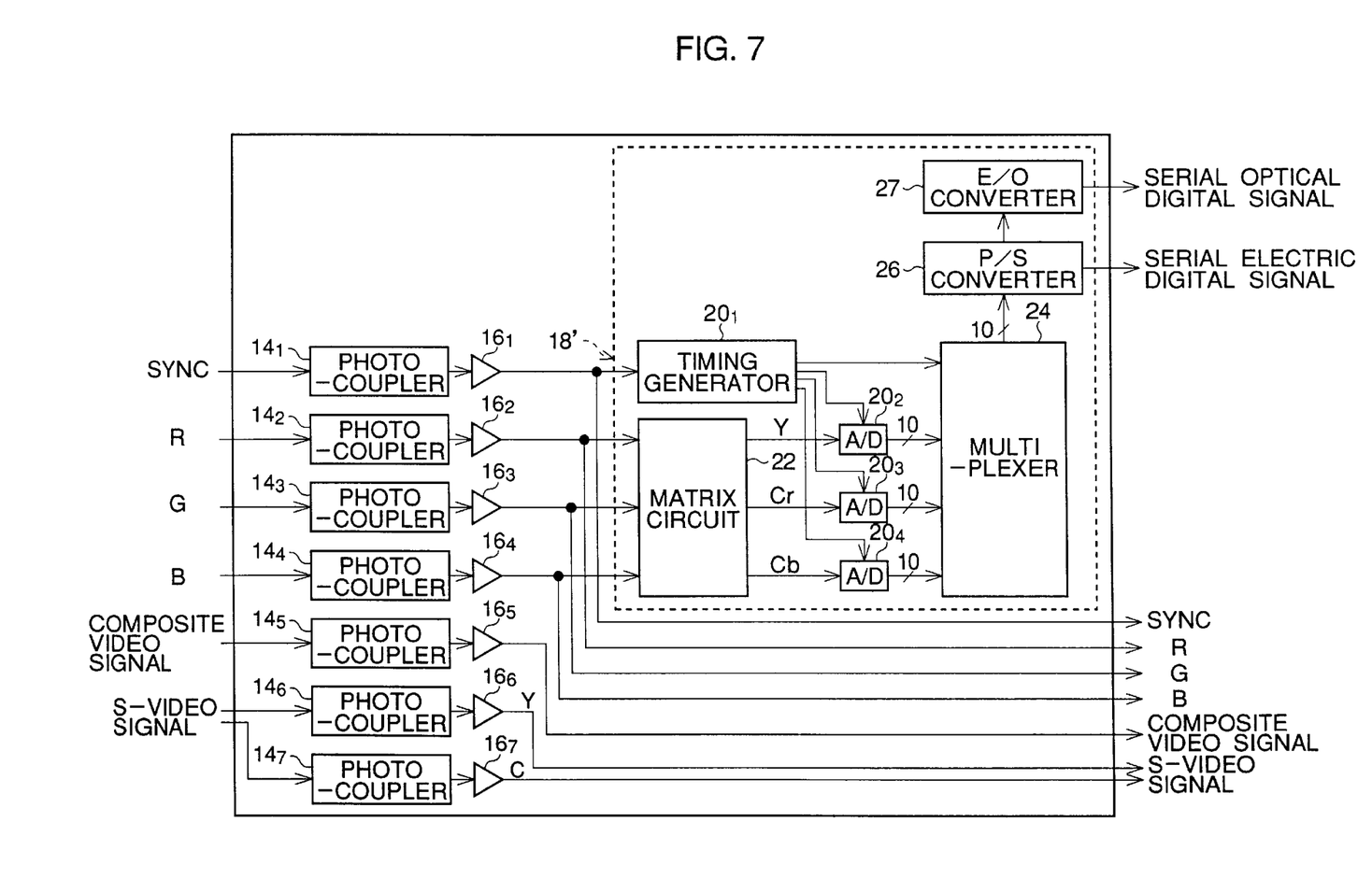
FIG. 7 is a block diagram showing a second embodiment of the video-signal processing device according to the present invention.

FIG. 7 shows a block diagram of a second embodiment of the video-signal processing device according to the present invention. In this drawing features similar to those of FIG. 2 are indicated by the same reference numerals. The second embodiment is similar to the first embodiment of FIG. 2' except that a digital-conversion processing circuit 18' of the second embodiment further includes an electrical-optical (E/O) converter 27 connected to the P/S converter 26 to convert the respective serial electric digital signals (Y, $C_r$, and $C_b$) into serial optical digital signals (Y, $C_r$, and $C_b$). Namely, in the second embodiment, the digital-conversion processing circuit 18 can output not only serial electric digital signals (Y, $C_r$, and $C_b$) but also-the-serial optical digital signals (Y, $C_r$, and $C_b$).

Figure 8:
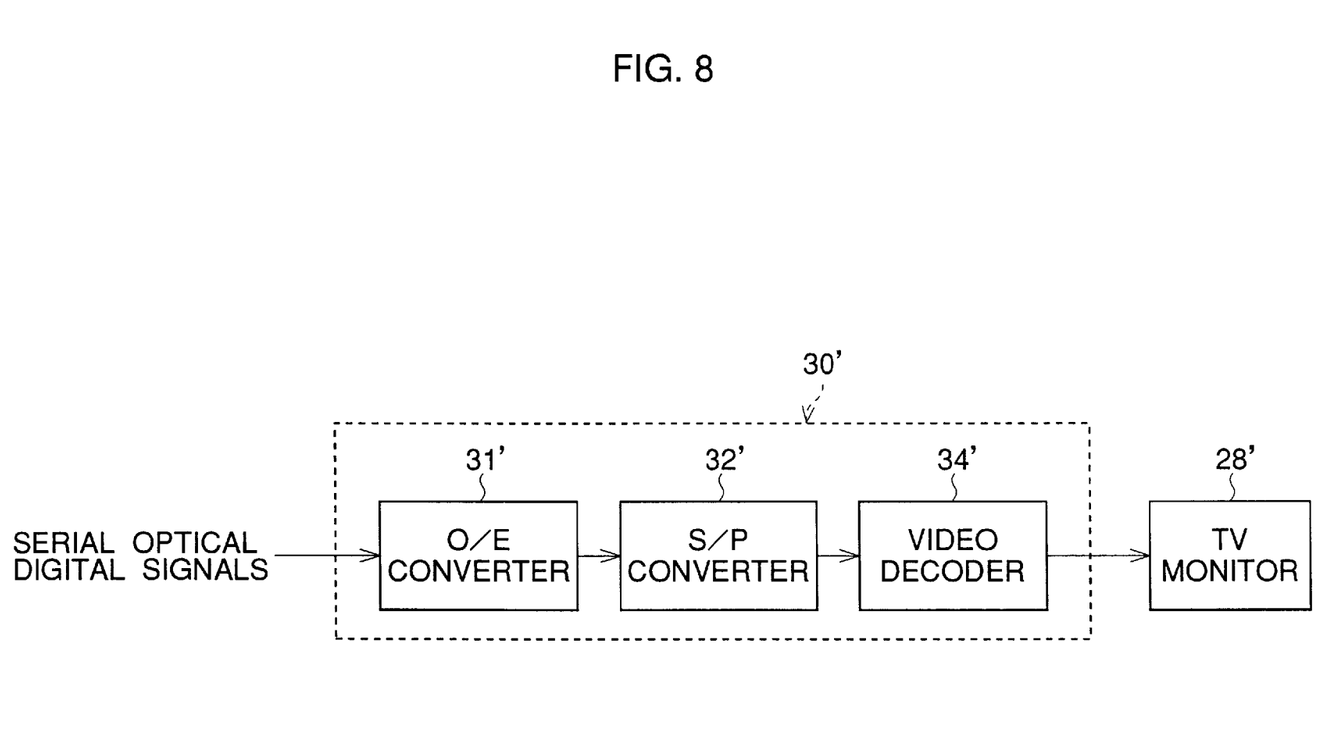
FIG. 8 is a block diagram of an analog-conversion processing circuit of a TV monitor to be connected to the video-signal processing device of FIG. 7.

FIG. 8 shows a TV monitor 28' as a peripheral, which is intended to be connected to the E/O converter 27 of the digital-conversion processing circuit 18' through an optical fiber cable. To this end, the TV monitor 28' is provided with an analog-conversion processing circuit 30', in which the respective serial optical digital signals (Y, $C_r$, and $C_b$) fed from the E/O converter 27 to the optical fiber cable are converted into an electric analog red video signal (R), an electric analog green video signal (G), and an electric analog blue video signal (B).

As shown in FIG. 8, the analog-conversion processing circuit 30' comprises an optical-electrical (O/E) converter 31', a serial-to-parallel (S/P) converter 32', and a video decoder 34'. It should be noted that the video decoder 34' is identical with the video decoder 34 shown in FIG. 6.

The serial optical digital signals (Y, $C_r$, and $C_b$) are sequentially fed from the E/O converter 27 to the analog-conversion processing circuit 30' in the order of the serial optical digital luminance signal (Y), the serial optical color-difference signal ($C_r$), the serial optical digital luminance signal (Y), and the serial optical digital color-difference signal ($C_b$). The serial optical digital signal (Y, $C_r$, $C_b$) fed to the analog-conversion processing circuit 30' is input to the O/E converter 31', which converts the serial optical digital signals (Y, $C_r$, $C_b$) into serial electric digital signals (Y, $C_r$, $C_b$).

The serial electric digital signals (Y, $C_r$, and $C_b$) outputted from the O/E converter 31' are input to the S/P converter 32', which converts the serial electric digital signals (Y, $C_r$, and $C_b$) into parallel electric digital signals (Y, $C_r$, and $C_b$). These parallel digital signals (Y, $C_r$, and $C_b$) output from the SP converter 32 are input to the video decoder 34', in which the parallel digital signals (Y, $C_r$, $C_b$) are processed in substantially the same manner as in the video decoder 34 (FIG. 6), whereby the video decoder 34' outputs an analog red vide signal (R), an analog green video signal (G), and an analog blue video signal (B) to the TV monitor 28' to thereby reproduce a color image thereon.

The optical fiber cable used to feed the serial optical digital signals (Y, $C_r$, and $C_b$) from the E/O converter 27 to the analog-conversion processing circuit 30' has a signal-feed loss lower than that of a coaxial cable used to feed the serial electric digital signals (Y, $C_r$, and $C_b$) from the P/S converter to the analog-conversion processing circuit 30 (FIG. 5). Accordingly, the second embodiment is preferred when peripheral equipment such as the TV monitor 28' is remote from the place where the electronic endoscope is used. Also, a peripheral such as the TV monitor 28' can be more securely insulated from the electronic endoscope by the optical fiber cable therebetween.

Figure 9:
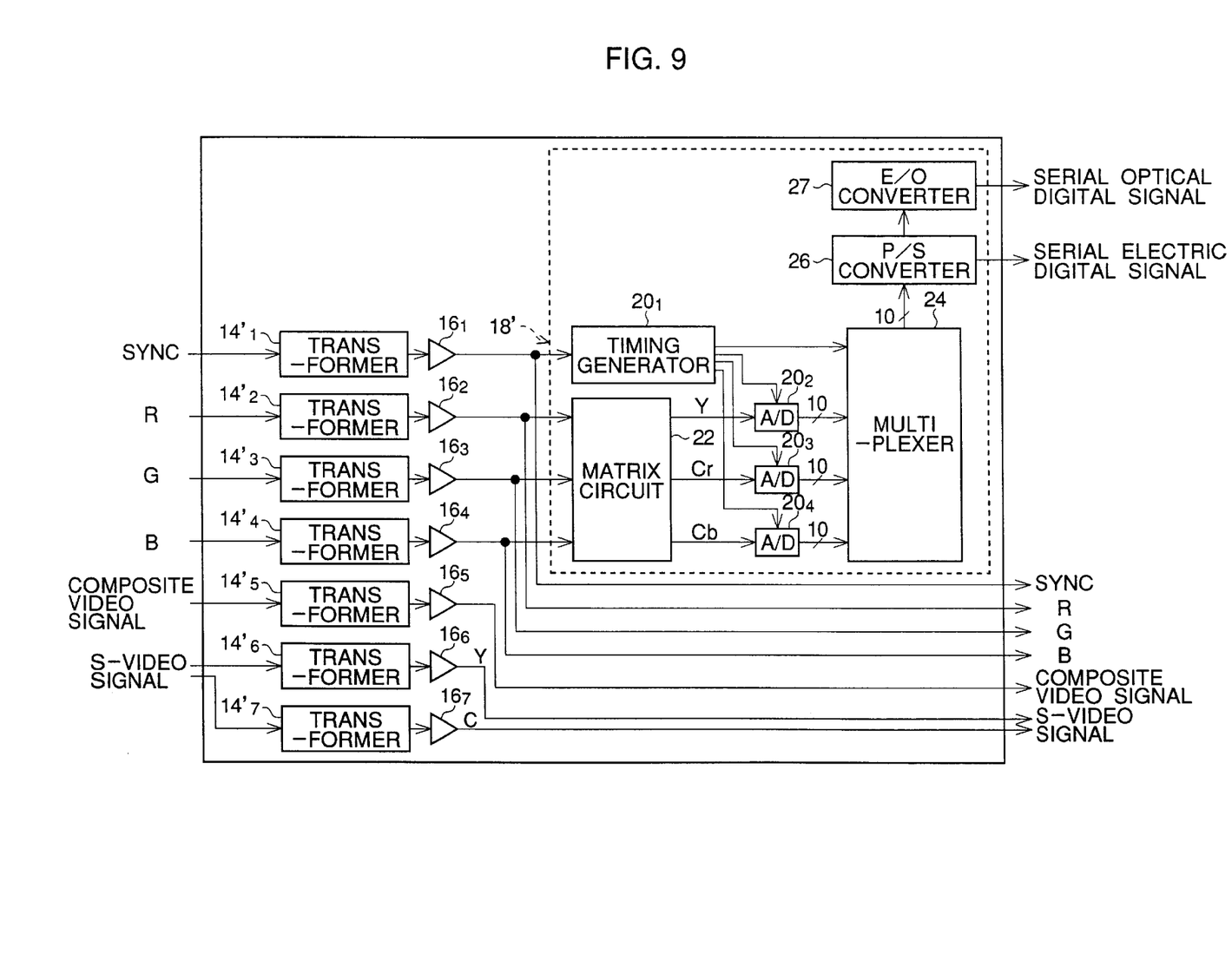
FIG. 9 is a block diagram showing a third embodiment of the video-signal processing device according to the present invention.

FIG. 9 shows a third embodiment of the video-signal processing device according to the present invention. In this drawing, features similar to those of FIG. 7 are indicated by the same reference numerals. The third embodiment is similar to the second embodiment of FIG. 7 except that seven transformers $14_1'$ to $14_7'$ are substituted for the photocouplers $14_1$ to $14_7$.

In the third embodiment, the respective primary windings of the transformers $14_1'$ to $14_7'$ are connected to the output lines of the video processor 12 of the electronic endoscope, and the respective secondary windings of transformers $14_1'$ to $14_7'$ are connected to the amplifiers $16_1$ to $16_7$. Thus, the electronic endoscope is electrically insulated from the video-signal processing device.

Figure 10:
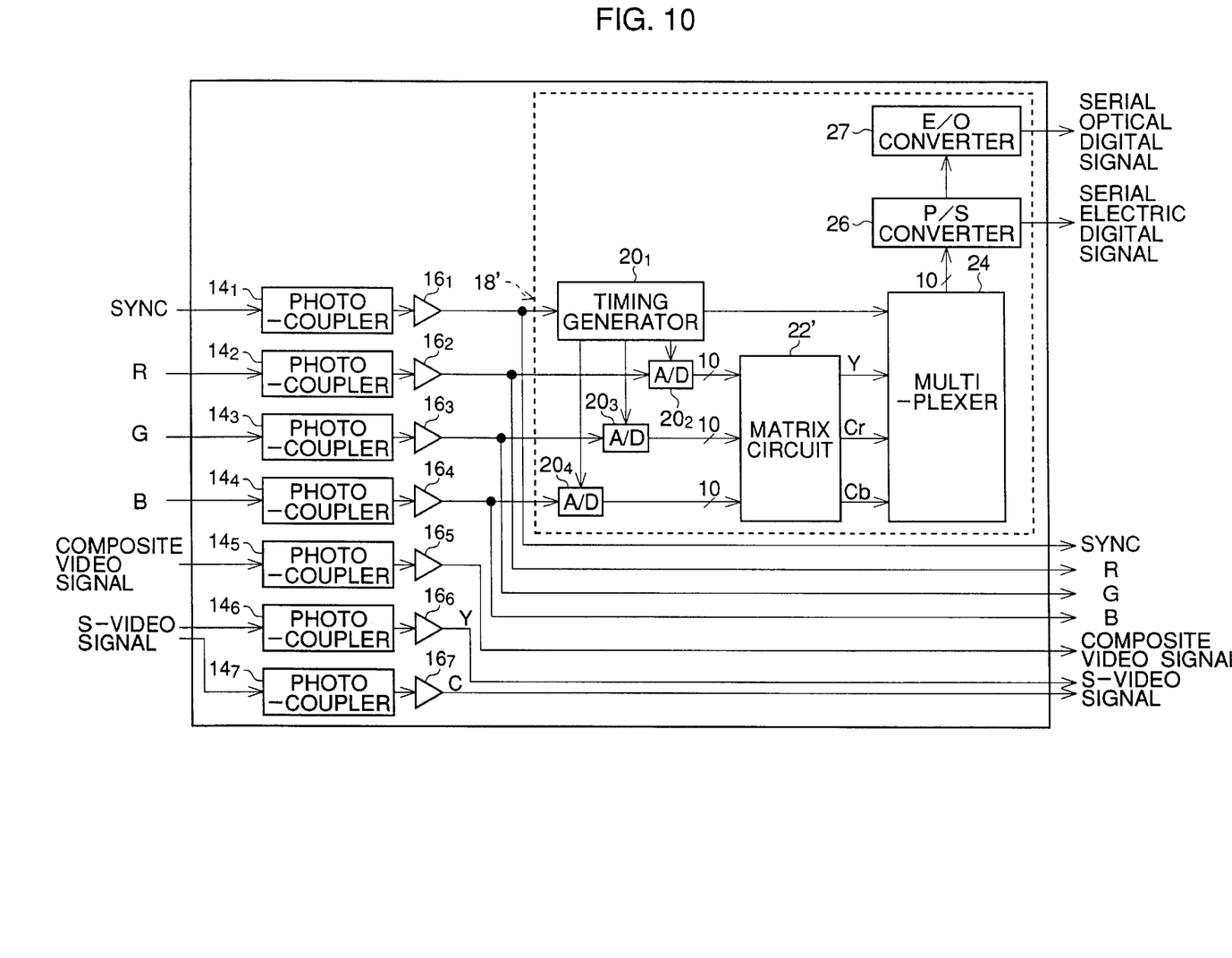
FIG. 10 is a block diagram showing a fourth embodiment of the video-signal processing device according to the present invention.

FIG. 10 shows a fourth embodiment of the video-signal processing device according to the present invention. In this drawing, features similar to those of FIG. 7 are indicated by the same reference numerals. The fourth embodiment is similar to the second embodiment of FIG. 7 except that a color-conversion digital matrix circuit 22' is substituted for the color-conversion analog matrix circuit 22, and is disposed between the A/D converters $20_2$ to $20_4$ and the multiplexer 24.

In the fourth embodiment, the respective red video signal (R), green vide signal (G), and blue video signal (B) output from the amplifiers $16_2$ to $16_4$ are input to the A/D converters $20_2$ to $20_4$, which convert the video signals (R, G, and B) into 10-bit digital signals (R, G, and B). Then, the respective 10-bit color digital video signal (R, G, and B) by outputted from the A/D converters 202 to 204 are input to the color-conversion digital matrix circuit 22', which produces a digital luminance signal (Y), and two kinds of digital color-difference signals $C_r$, $C_b$ ($C_r$=R−Y and $C_b$=B−Y) on the basis of the input color digital video signals (R, G, and B). Thus, the 10-bit digital luminance signal (Y), and the two kinds of 10-bit color-difference signals ($C_r$ and $C_b$) are processed in substantially the same manner as mentioned above.

Figure 11:
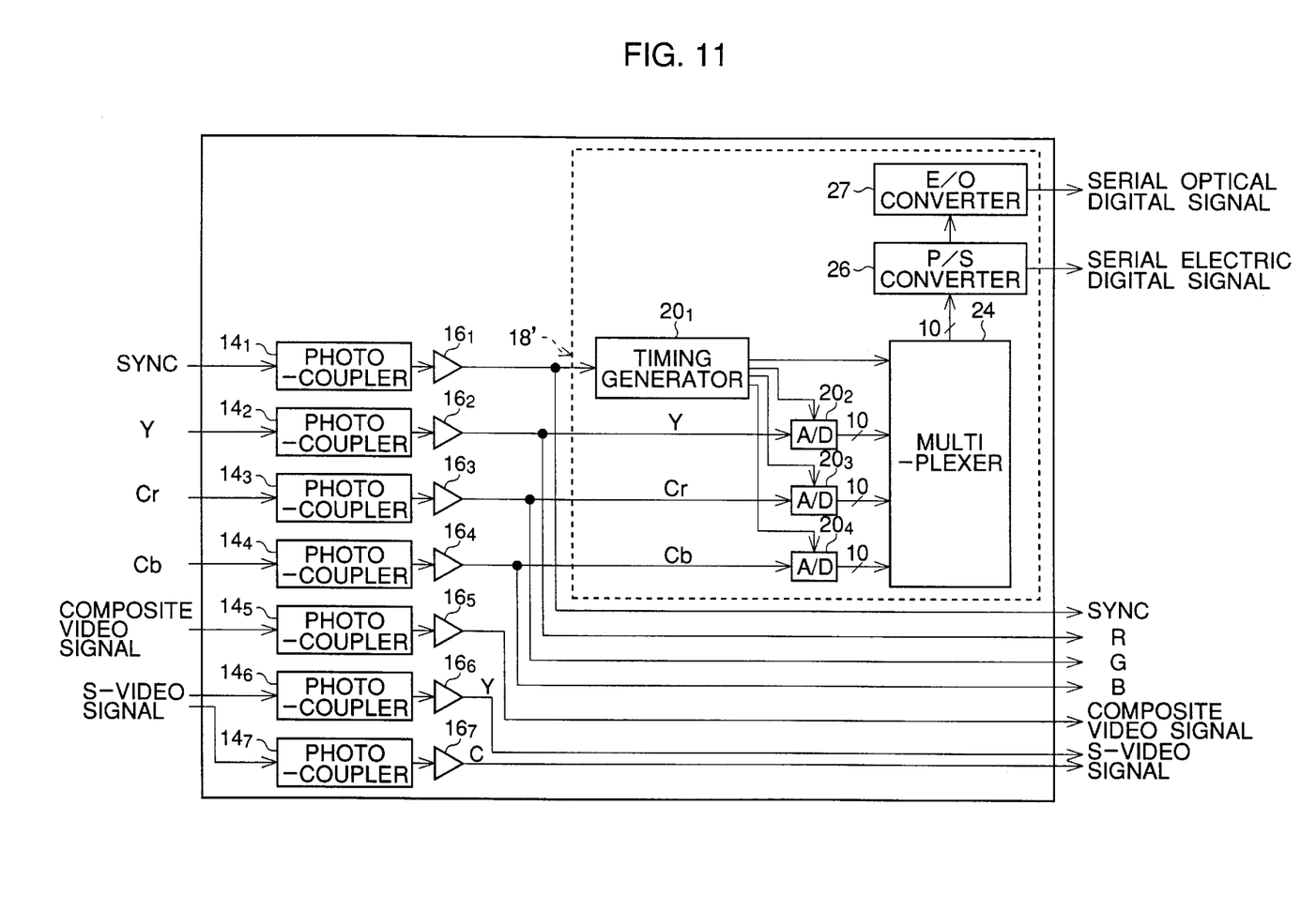
FIG. 11 is a block diagram showing a fifth embodiment of the video-signal processing device according to the present invention.

FIG. 11 shows a fifth embodiment of the video-signal processing device according to the present invention. In this drawing, features similar to those of FIG. 7 are indicated by the same reference numerals. The fifth embodiment is similar to the second embodiment of FIG. 7 except that the color-conversion analog matrix circuit 22 is eliminated therefrom.

The fifth embodiment is connectable to an electronic endoscope that outputs a component-type color video signal including a luminance signal (Y), and two kinds of color-difference signals ($C_r$ and $C_b$), from its video processor. Thus, in the fifth embodiment, the color-conversion analog matrix circuit (22) is unnecessary.

Finally, it will be understood by those skilled in the art that the foregoing description is of preferred embodiments of the device and that various changes and modifications may be made to the present invention without departing from the spirit and scope thereof.

The present disclosure relates to subject matter contained in Japanese Patent Application no. 8-106183 (filed on Apr. 3, 1996), which is expressly incorporated herein, by reference, in its entirety.

What is claimed is:

1. A video-signal processing device connectable to a video processor of an electronic endoscope, comprising:

an insulation coupler that intercepts an electric analog video signal of the video processor of the electronic endoscope and that electrically insulates the video processor of the electronic endoscope from said device;

an analog-to-digital converter that converts the electric analog video signal into a parallel electric digital video signal; and a parallel-to-serial converter that converts the parallel electric digital video signal into a serial electric digital video signal, and that feeds the serial electric digital video signal from the video-signal processing device to a piece of compatible external digital peripheral equipment, wherein said insulation coupler output is split and the electric analog video signal is sent to the analog-to-digital converter and to at least one piece of analog peripheral equipment.

2. A video-signal processing device as set forth in claim 1, wherein said insulation coupler is a photo-coupler.

3. A video-signal processing device as set forth in claim 1, wherein said insulation coupler is a transformer coupler.

4. A video-signal processing device as set forth in claim 1, further comprising an electrical-optical converter that converts the serial electric digital video signal into a serial optical digital video signal.

5. A video-signal processing device as set forth in claim 1, wherein said insulation coupler is a photo-coupler.

6. A video-signal processing device connectable to a video processor of an electronic endoscope, comprising:
   an insulation coupler that receives at least one kind of electric analog video signal, obtained from the electronic endoscope, and that electrically insulates all electrical connections of the electronic endoscope to said device;
   an analog-to-digital converter that converts the at least one kind of electric analog video signal into a parallel electric digital video signal; and
   a parallel-to-serial converter that converts the parallel electric digital video signal into a serial electric digital video signal, and that feeds the serial electric digital video signal from the video-signal processing device to a piece of compatible external digital peripheral equipment,
   wherein said insulation coupler output is split and the at least one kind of electric analog video signal is sent to the analog-to-digital converter and to at least one piece of analog peripheral equipment.

7. A video-signal processing device as set forth in claim 6, wherein said insulation coupler is a transformer coupler.

8. A video-signal processing device as set forth in claim 6, further comprising an electrical-optical converter that converts the serial electric digital video signal into a serial optical digital video signal.

9. A video-signal processing device connectable to a video processor of an electronic endoscope, comprising:
   respective insulation couplers that intercept electric signal-components of the video processor of the electronic endoscope and that electrically insulate all electrical connections of the video processor of the electronic endoscope to said device;
   an analog-to-digital converter that converts each of the electric signal-components into a parallel electric digital signal-component; and
   a parallel-to-serial converter that converts the parallel electric digital signal-components into a serial digital component-type color video signal, and that feeds the serial digital component-type color video signal from the video-signal processing device to a piece of compatible external digital peripheral equipment,
   wherein said insulation couplers outputs are split and the electric signal components are sent to the analog-to-digital converter and to at least one piece of analog peripheral equipment.

10. A video-signal processing device as set forth in claim 9, wherein each of said insulation couplers is a photo-coupler.

11. A video-signal processing device as set forth in claim 9, wherein each of said insulation couplers is a transformer coupler.

12. A video-signal processing device as set forth in claim 9, further comprising an electrical-optical converter that converts the serial electric digital signal-component into a serial optical digital signal-component.

13. A video-signal processing device connectable to a video processor of an electronic endoscope, comprising:
   respective insulation couplers that receive at least one kind of analog component-type color video signal comprising at least three electric signal-components, obtained from the electronic endoscope, the respective electric signal-components being a red video signal-component, a green video signal-component, and a blue video signal-component, and said insulation couplers electrically insulate all electrical connections of the video processor of the electronic endoscope to said device;
   a color-conversion analog matrix that produces a luminance signal-component, and two kinds of color-difference signal-components on the basis of the red, green and blue video signal-components;
   an analog-to-digital converter that converts each of the luminance signal-components and the two kinds of color-difference signal-components into a parallel electric digital signal-component; and
   a parallel-to-serial converter that converts the parallel electric digital signal-components into a serial digital component-type color video signal, and that feeds the serial digital component-type color video signal from the video-signal processing device to a piece of compatible external digital peripheral equipment,
   wherein said insulation couplers outputs are split and the at least one kind of analog component-type color video signal is sent to the color-conversion analog matrix and to at least one piece of analog peripheral equipment.

14. A video-signal processing device as set forth in claim 13, further comprising an electrical-optical converter for converting the serial digital component-type color video signal into a serial optical digital component-type color video signal.

15. A video-signal processing device connectable to a video processor of an electronic endoscope, comprising:
   respective insulation couplers that receive at least one kind of analog component-type color video signal comprising at least three electric signal-components, obtained from the electronic endoscope, the respective electric signal-components being a red video signal-component, a green video signal-component, and a blue video signal-component, and said respective insulation couplers electrically insulate all electrical connections of the video processor of the electronic endoscope to said device;
   an analog-to-digital converter that converts each of the red, green, and blue video signal-components into a parallel digital color signal-component;
   a color-conversion digital matrix that produces a parallel luminance signal-component, and two kinds of parallel color-difference signal-components on the basis of the parallel digital color signal-components; and
   a parallel-to-serial converter that converts the parallel luminance signal-component and the two kinds of parallel color difference signal-components into a serial digital component-type color video signal, and that feeds the serial digital component-type color video signal from the video-signal processing device to a piece of compatible external digital peripheral equipment,
   wherein said insulation couplers outputs are split and the at least one kind of analog component type color video signal is sent to the analog-to-digital converter and to at least one piece of analog peripheral equipment.

16. A video-signal processing device as set forth in claim 15, further comprising an electrical-optical converter that converts the serial digital component-type color video signal into a serial optical digital component-type color video signal.

* * * * *